(12) United States Patent
Swanson et al.

(10) Patent No.: US 8,271,098 B2
(45) Date of Patent: Sep. 18, 2012

(54) METHOD FOR PROCESSING ELECTRODES FOR STIMULATION LEAD

(75) Inventors: John Swanson, Portland, OR (US); Anna Norlin-Weissenrieder, St. Paul, MN (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 327 days.

(21) Appl. No.: 12/604,251

(22) Filed: Oct. 22, 2009

(65) Prior Publication Data

US 2010/0100165 A1     Apr. 22, 2010

Related U.S. Application Data

(60) Provisional application No. 61/107,378, filed on Oct. 22, 2008.

(51) Int. Cl.
*A61N 1/05* (2006.01)
(52) U.S. Cl. .................. 607/117; 607/115; 607/116
(58) Field of Classification Search ........... 607/115–122
See application file for complete search history.

(56) References Cited

U.S. PATENT DOCUMENTS

| | | | |
|---|---|---|---|
| 4,649,937 A | 3/1987 | DeHaan et al. | |
| 5,318,572 A | 6/1994 | Helland et al. | |
| 5,330,700 A | 7/1994 | Soukup et al. | |
| 7,351,921 B1 | 4/2008 | Haller et al. | |
| 2003/0083724 A1* | 5/2003 | Jog et al. | 607/122 |
| 2003/0195601 A1 | 10/2003 | Hung et al. | |
| 2004/0006396 A1 | 1/2004 | Ricci et al. | |
| 2005/0137669 A1 | 6/2005 | Krishnan et al. | |
| 2007/0265691 A1* | 11/2007 | Swanson | 607/117 |
| 2007/0265692 A1 | 11/2007 | Koop et al. | |

FOREIGN PATENT DOCUMENTS

WO     2009111142     9/2009

OTHER PUBLICATIONS

European Patent Office, International Search Report for PCT/US2009/061706 dated Jul. 13, 2011.
M Schuettler, et al., "Fabrication of implantable microelectrode arrays by laser cutting of silicone rubber and platinum foil," Journal of Neural Engineering, 2005, vol. 2, pp. S121-S128.
Australian Government, Examiner's first report for AU Innovation Patent No. 2011100508, mailed Nov. 18, 2011.

* cited by examiner

*Primary Examiner* — Rex R Holmes
(74) *Attorney, Agent, or Firm* — Craig Hoersten; Christopher S. L. Crawford; Peter R. Lando

(57) ABSTRACT

In one embodiment, a method, of fabricating a stimulation lead for stimulating tissue of a patient, comprises: providing a lead body, the lead body comprising a plurality of conductors embedded within insulating material; providing a plurality of terminals; electrically coupling the plurality of terminals with the plurality of conductors; providing a plurality of electrodes, the plurality of electrodes comprising a plurality of substantially continuous longitudinal trenches on a surface of the electrodes, the electrodes comprising areas of reflow material forming microstructures substantially continuously along walls of the longitudinal trenches; and electrically coupling the plurality of electrodes with the plurality of conductors.

15 Claims, 6 Drawing Sheets

METHOD FOR PROCESSING ELECTRODES FOR STIMULATION LEAD

CROSS-REFERENCE TO RELATED APPLICATIONS

This application claims the benefit of U.S. Provisional Application No. 61/107,378, filed Oct. 22, 2008, which is incorporated herein by reference.

TECHNICAL FIELD

The application is generally related to electrical stimulation leads including electrodes having relatively high surface area characteristics and methods of processing electrodes to possess such characteristics.

BACKGROUND

Neurostimulation systems are devices that generate electrical pulses and deliver the pulses to nerve tissue to treat a variety of disorders. Spinal cord stimulation (SCS) is an example of neurostimulation in which electrical pulses are delivered to nerve tissue in the spine typically for the purpose of chronic pain control. Other examples include deep brain stimulation, cortical stimulation, cochlear nerve stimulation, peripheral nerve stimulation, vagal nerve stimulation, sacral nerve stimulation, etc. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

Neurostimulation systems generally include a pulse generator and one or more leads. The pulse generator is typically implemented using a metallic housing that encloses circuitry for generating the electrical pulses, control circuitry, communication circuitry, a rechargeable battery, etc. The pulse generation circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead. The terminals of a stimulation lead are electrically coupled to conductors disposed within the insulative body of the stimulation lead. Electrodes are also electrically coupled to the conductors on a distal end of the stimulation lead. Electrical pulses are conducted from the pulse generating circuitry through the feedthrough wires, the annular connectors, the terminals, and the conductors to the electrodes to stimulate tissue of the patient.

The charge transfer characteristics of electrodes are important in avoiding degradation of the conductive material of the electrodes and in avoiding injury to tissue of the patient. Specifically, when implanted within a patient, the electrodes of a stimulation lead are essentially immersed in aqueous solution. Application of electrical current through the conductive material in such an environment may compromise their chemical stability by promoting corrosion and degradation. Corrosion of the stimulation electrode may lead to premature failure of the stimulation lead and adverse tissue reactions triggered by the release of corrosion products. In addition, an adverse tissue response may be trigged by irreversible faradaic reactions (such as electrolysis of water). In general, neurostimulation systems limit the current density of stimulation pulses to avoid these issues.

In one embodiment, a method, of fabricating a stimulation lead for stimulating tissue of a patient, comprises: providing a lead body, the lead body comprising a plurality of conductors embedded within insulative material; providing a plurality of terminals; electrically coupling the plurality of terminals with the plurality of conductors; providing a plurality of electrodes, the plurality of electrodes comprising a plurality of substantially continuous longitudinal trenches on a surface of the electrodes, the electrodes comprising areas of reflow material forming microstructures substantially continuously along walls of the longitudinal trenches; and electrically coupling the plurality of electrodes with the plurality of conductors.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

Figure 1A:
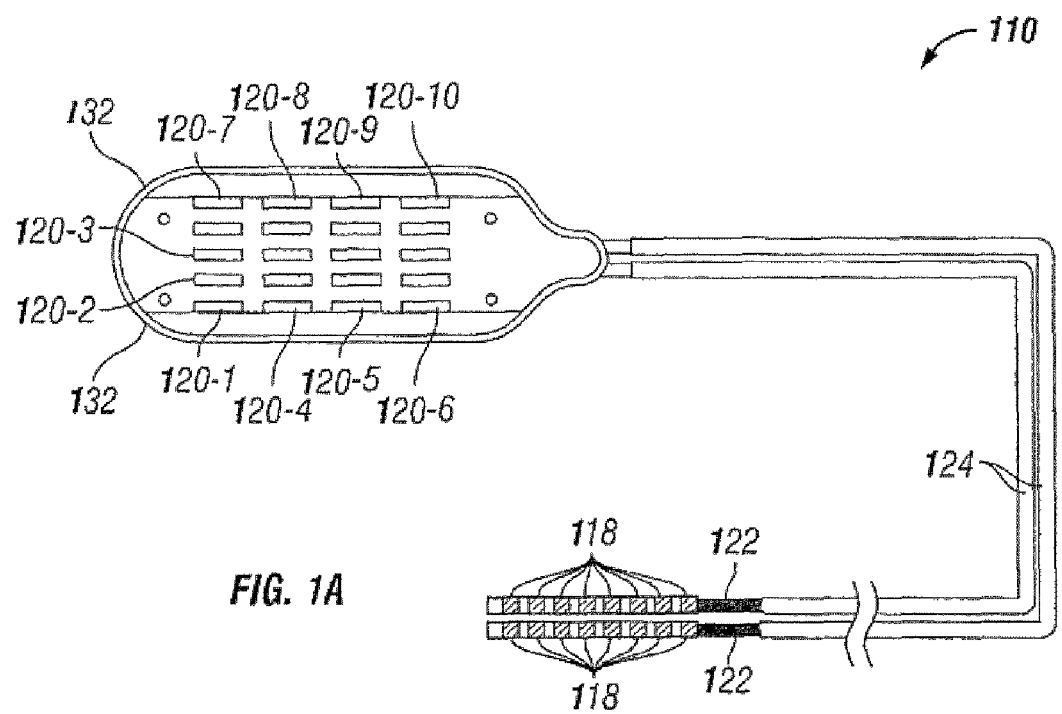
FIG. 1A depicts an example laminotomy or paddle lead according to one representative embodiment.

FIG. 1A depicts an example laminotomy or paddle lead 110 according to one representative embodiment. Laminotomy lead 110 includes a proximal end and a distal end. The proximal end includes a plurality of electrically conductive terminals 118. The distal end includes a plurality of electrically conductive electrodes 120 (only electrodes 120-1 through 120-10 are annotated for the sake of clarity) arranged within a flat, thin paddle-like structure. The electrodes 120 are mutually separated by insulative material of the paddle. For a paddle structure adapted for implantation within a cervical vertebral level, the electrodes are preferably spaced apart 1.5 mm laterally and 2.5 mm longitudinally. The length of each electrode is preferably approximately 4.0 mm and the width of each electrode is preferably approximately 1.0 mm thereby providing a geometrical surface area of approximately 4.0 mm$^2$. For a paddle adapted for implantation within a thoracic vertebral level, the electrodes are preferably spaced apart by 1.0 mm laterally and 2 mm or 3 mm longitudinally. Conductors 122 (which are embedded within the insulative material of the lead body) electrically connect electrodes 120 to terminals 118.

In the specific example shown in FIG. 1A, the paddle includes five columns and four rows of electrodes 120. Alternative numbers of columns and rows may be employed. The multiple columns of electrodes enable lateral control of the applied electrical field to stimulate the exact lateral position of the pertinent nerve fiber(s). Specifically, it is desirable to selectively stimulate respective dorsal column fibers that are associated with an afflicted region of the patient's body without affecting other regions of the patient's body. The multiple columns of electrodes according to representative embodiments provide sufficient resolution to relatively finely control the stimulation of one or several specific fibers. Additionally, the multiple columns provide a degree of positional tolerance during the surgical placement of the paddle within the epidural space, because any one of the columns can be used to stimulate the pertinent nerve fiber(s). Also, if the paddle is displaced relative to the pertinent nerve fibers subsequent to implantation (e.g., due to lead migration), the stimulation pattern applied by the pulse generator can be shifted between columns to compensate for the displacement.

In some embodiments, paddle lead 110 is adapted to be implanted within a patient such that the electrodes are positioned within a cervical vertebral level or a relatively high thoracic vertebral level. A benefit of implanting paddle lead 100 within a relatively high vertebral level is the ability to obtain paresthesia over a relatively large range of regions of the patient's body. For example, a first row can be used to treat a first pain location (e.g., pain in the lower extremities) and a second row can be used to treat a second pain location (e.g., post-laminectomy pain in the back) which could otherwise conventionally require multiple stimulation leads if implanted in other vertebral levels.

Preferably, after implantation, one or more electrode combinations on a first row of electrodes can be determined that is effective for a first pain location with minimal effects on other regions of the body. The first pain location can be addressed by stimulating specific dorsal column fibers due to the relatively fine electrical field resolution achievable by the multiple columns. Then, one or more electrode combinations on a second row of electrodes can be determined for a second pain location with minimal effects on other regions of the body. The second pain location could be addressed by stimulating other specific dorsal column fibers as an example. Preferably, a degree in selectivity in stimulating dorsal column fibers is provided when selecting the one or more electrode combinations for the respective rows to limit paresthesia to the specific bodily regions.

The selectivity in stimulating respective dorsal column fibers can be facilitated by "steering" of the electrical field. Steering may occur using any suitable technique known in the art. For example, closely timed (non-overlapping temporally) stimulation pulses on different electrode combinations may be used to shift the locus of stimulation laterally using a single-source implantable pulse generator. Alternatively, simultaneous or overlapping application of stimulation pulses using different electrode combinations may be used to shift the locus of stimulation when a multi-source implantable pulse generator is employed. Anodal blocking may also be utilized to select anode states for selected electrodes as is known in the art.

Conductors 122 are carried or embedded in the insulative material of sheaths or lead bodies 124. In some embodiments, each sheath 124 carries eight conductors 122. With only two sheaths 124 with eight conductors each, there would only be sixteen conductors 122. To accommodate the lower number of conductors 122 than electrodes 120, multiple electrodes 120 are coupled to the same conductor 122 (and, hence, to a common terminal 118). In one embodiment, electrodes 120-1 and 120-4 are coupled to a common conductor 122, electrodes 120-5 and 120-6 are coupled to a common conductor 122, electrodes 120-7 and 120-8 are coupled to a common conductor, and electrodes 120-9 and 120-10 are coupled to a common conductor.

In some embodiments, other electrode designs can be employed to minimize the number of conductors 122 required to support the various electrodes 120. For example, a relatively large number of electrodes (e.g., thirty-two, sixty-four, and greater) could be utilized on the paddle structure. The electrodes could be coupled to one or several electrical gates (e.g., as deposited on a flex circuit). The electrical gates can be controllably configured to couple each electrode to a conductor 122 carrying cathode pulses, to couple each electrode to an anode termination, or to maintain each electrode at a high impedance state. The electrical gates could be controlled using a main controller (a logic circuit) on the paddle structure that is coupled to a data line conductor 122. The data line conductor 122 is used to communicate signals from the IPG that identify the desired electrode states. The main controller responds to the signals by setting the states of the electrical gates as appropriate.

Terminals 118 and electrodes 120 are preferably formed of a non-corrosive, highly conductive material. Examples of such material include stainless steel, MP35N, platinum, and platinum alloys. In a preferred embodiment, terminals 118 and electrodes 120 are formed of a platinum-iridium alloy. Each conductor 122 is formed of a conductive material that exhibits desired mechanical properties of low resistance, corrosion resistance, flexibility, and strength. While conventional stranded bundles of stainless steel, MP35N, platinum, platinum-iridium alloy, drawn-brazed silver (DBS) or the like can be used, a preferred embodiment uses conductors 122 formed of multi-strands of drawn-filled tubes (DFT). Each strand is formed of a low resistance material and is encased in a high strength material (preferably, metal). A selected number of "sub-strands" are wound and coated with an insulative material. With regard to the operating environment of representative embodiments, such insulative material protects the individual conductors 122 if its respective sheath 124 was breached during use.

Sheaths 124 and the paddle structure of lead 110 are preferably formed from a medical grade, substantially inert material, for example, polyurethane, silicone, or the like. Importantly, such material should be non-reactive to the environment of the human body, provide a flexible and durable (i.e., fatigue resistant) exterior structure for the components of lead 110, and insulate adjacent terminals 118 and/or electrodes 120. Additional structure (e.g., a nylon mesh, a fiberglass substrate) (not shown) can be internalized within the paddle structure to increase its overall rigidity and/or to cause the paddle structure to assume a prescribed cross-sectional form.

Figure 1B:
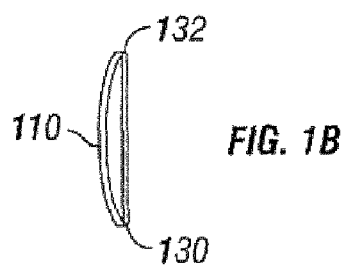
FIG. 1B depicts a cross-sectional profile that can be used for the paddle lead shown in FIG. 1A according to one representative embodiment.
Figure 2A:
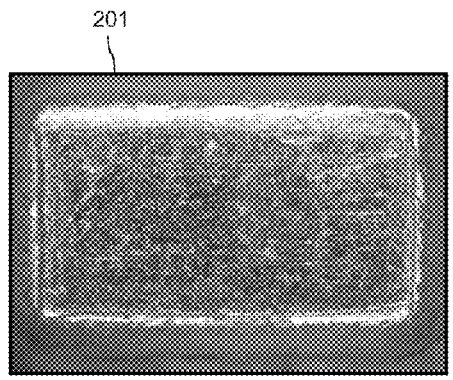
FIG. 2A depicts a conventional surface texture of an electrode and FIGS. 2B-2D depict respective electrodes of platinum iridium having respective surface textures according to some representative embodiments.
Figure 2B:
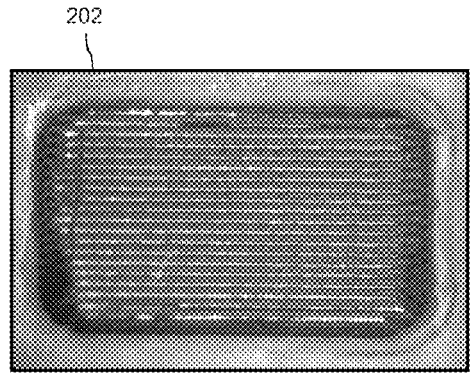
Figure 2C:
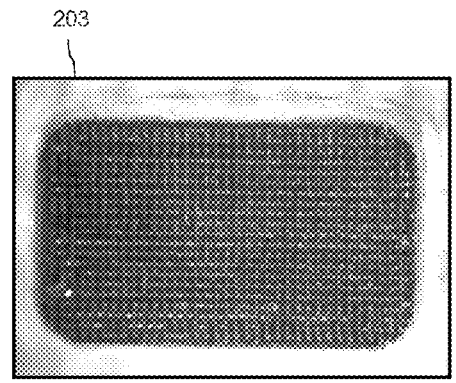
Figure 2D:
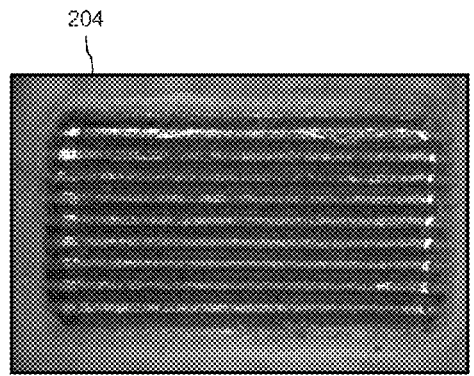
Figure 3A:
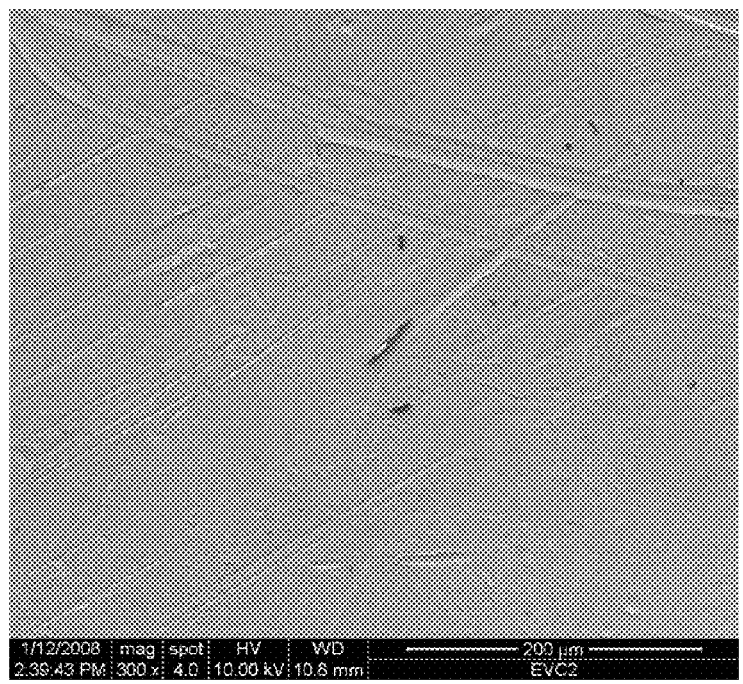
FIGS. 3A-3F depict SEM images of the surface textures of the electrodes shown in FIGS. 2A-2D.
Figure 3B:
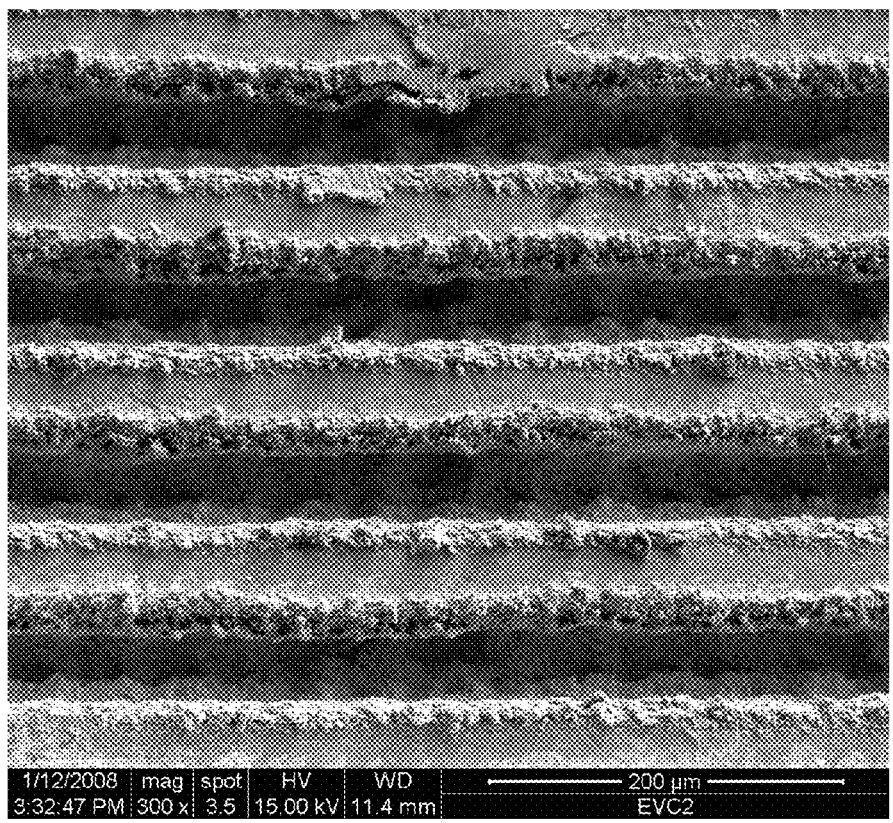
Figure 3C:
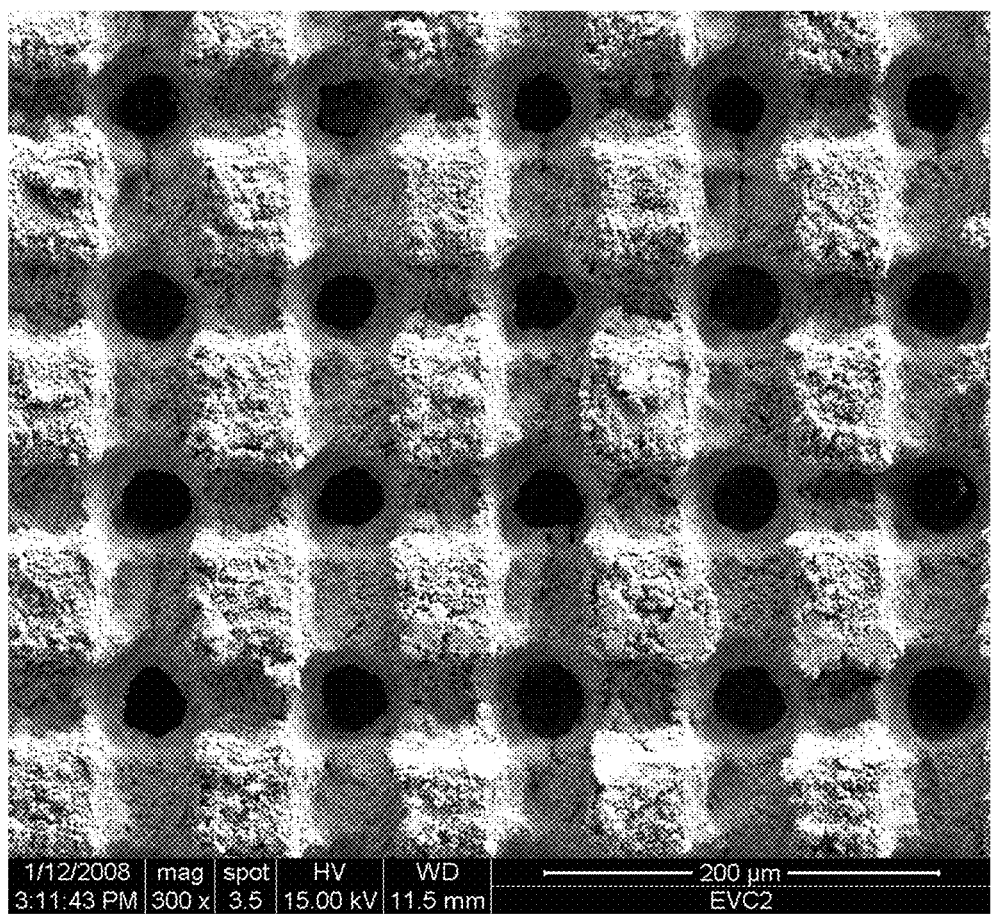
Figure 3D:
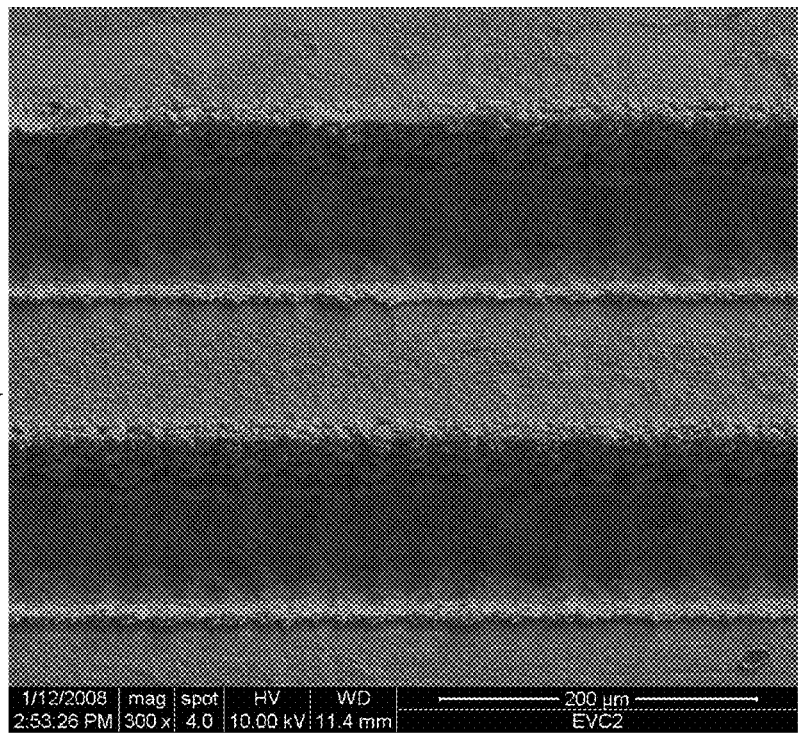
Figure 3E:
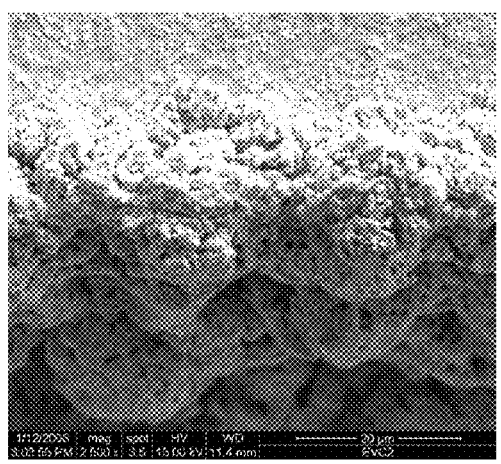
Figure 3F:
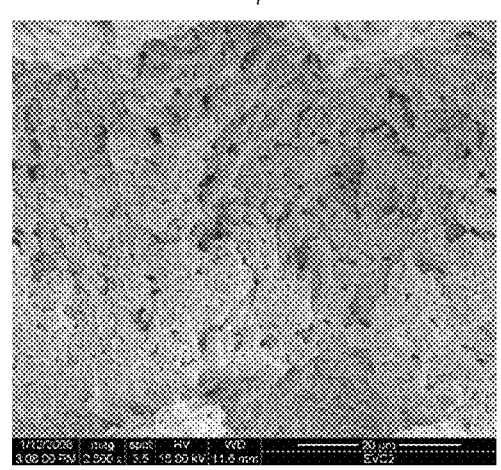

The paddle structure may be fabricated to possess a substantially flat profile. As one alternative, the paddle structure may be fabricated to possess a prescribed arc along a transverse or lateral direction of the paddle structure as shown in the cross-sectional view of FIG. 1B. On each longitudinal side of the paddle structure, "wing" structures 130, 132 may be formed for the purpose of retaining the paddle structure within the central portion of the epidural space. In some embodiments, one or several electrodes 120 could be disposed on the wing structures 130, 132.

While a number of material and construction options have been discussed above, it should be noted that neither the materials selected nor a construction methodology is critical to the present invention.

Although the number of rows of electrodes enables a greater degree of flexibility in treating neurological disorders, the number of rows reduces the possible surface area for the electrodes of lead 110. For the reasons previously discussed, conventional IPGs limit the amount of current applied to tissue by electrodes to prevent electrode damage or degradation and to prevent adverse tissue reactions. The use of electrodes with smaller surface area and conventional surface characteristics further limits the amount of current that would be typically provided by an IPG. In view of such limitations for conventional IPGs and conventional electrodes, it may not be possible to sufficiently stimulate neural tissue associated with a particular patient disorder. For example, if the maximum stimulation current is unduly limited, it may not be possible to stimulate deeper dorsal column fibers with a conventional IPG and conventional electrodes at a relatively high vertebral level to obtain paresthesia for a particular region of the patient's body that is afflicted by chronic pain.

Some embodiments compensate for the reduction in surface area by processing the electrode surface to improve the charge transfer characteristics of electrodes 120. In one embodiment, paddle lead 110 is constructed using electrodes 120 of platinum alloyed with 10% iridium. Each electrode is laser micro-machined to provide a surface texture that comprises a plurality of surface features. In this preferred embodiment, an ESI 4420 YAG laser is operated at 266 nm, 300 mW, and 2 kHz, with a transverse rate of 10 mm/sec over multiple passes over the electrodes to produce the respective features. In one embodiment, longitudinal channels or trenches are formed, having a width of about 100 micron and a depth of about 100 micron. In other embodiments, the width can range from 25-100 microns and the depth can range from 25-100 microns.

FIGS. 2A-2D depict respective electrodes 201-204 of platinum iridium alloy having respective surface textures. Each electrode 201-204 comprises a geometrical surface area of 0.06 cm$^2$ (2 mm×3 mm). The surface texture of electrode 201 is the conventional surface texture of electrodes utilized in typical neurostimulation paddle-style leads. The surface textures of electrodes 202 and 204 are defined by linear channels or trenches formed along the length of electrodes 202 and 204 using the ESI 4420 YAG laser as discussed above. The width of these channels are 0.02 inches and 0.04 inches respectively. Electrode 203 comprises a cross-hatched surface area formed by machining respective sets of linear channels in opposing directions. Using such machining, electrode 203 possesses the greatest increase in geometrical surface area, while electrode 202 possesses the least, and electrode 204 possesses an intermediate amount.

FIGS. 3A-3F depict SEM images 301-306 of the surface textures of electrodes 201-204. Images 301-303 correspond to electrodes 201-203, respectively. Images 304-306 are images of electrode 204 at multiple magnification levels. In addition to the macroscopic surface features, the laser machining of electrodes 202-204 creates surface microstructure roughness as shown in FIGS. 3B-3F. The roughness of the electrode surfaces most likely results from the creation of locally high temperatures within or adjacent to the laser machined channels. The microstructure roughness caused by such high temperatures is referred to as "reflow material" herein. The microscopic surface features are present within the machined trenches and, in some cases, extend over the edges of the trenches.

Electrodes 201-204 were subjected to electrochemical analysis. The analysis of the electrodes included determining the relative surface area of the electrodes by electrochemical impedance spectroscopy (EIS). Even though the distance between trenches in electrodes 202 and 203 is smaller and, hence, electrodes 202 and 203 possess a greater number of trenches, these electrodes did not possess the greatest amount of total surface area. Instead, electrode 204 exhibited the greatest surface area. Quantitatively, electrodes 202, 203, and 204 exhibited surface area increases by factors' of 36, 52, and 111, respectively relative to the surface area of electrode 201.

Electrodes 201-204 were also subjected to constant potential pulses and the current resulting from the pulses was measured. Following the trend in the effective surface area data, electrode 201 exhibited the lowest current delivery capacity while electrode 204 exhibited the highest current delivery capacity. Electrodes 202 and 203 exhibited intermediate current delivery capacity.

Electrodes 201-204 were further subjected to relatively high amplitude constant current pulses and the resulting potentials on the electrodes were measured. Electrode 201 exhibited the propensity for exceeding the biologically safe cathodic potential. Specifically, it was observed that the potential present on electrode 201 could exceed the potential necessary for irreversible chemical reactions to occur. The surface textures of electrodes 202-204 reduced the possibility of exceeding biologically safe potential levels for constant current pulses.

By processing electrode surfaces using laser machining according to some representative embodiments, superior stimulation performance may be achieved. At lower stimulation currents, the amount of energy required from the pulse generator may be lowered as lower potentials are required to source the necessary current. Also, the possibility of damage to the electrode surfaces and adverse tissue reactions may be reduced as the electrode potential is maintained under the safe potential levels even when relatively higher current stimulation pulses are employed.

Although preferred embodiments provide electrodes for neurostimulation leads, electrical leads for other medical applications may employ laser machined electrodes. For example, cardiac leads or gastric stimulation leads may employ electrodes according to some representative embodiments. Also, although paddle leads have been described according to some embodiments, ring electrodes could be laser machined for use in percutaneous leads according to other embodiments. For example, trenches could be laser machined in a circumferential manner about a ring electrode to increase its effective surface area.

Figure 4:
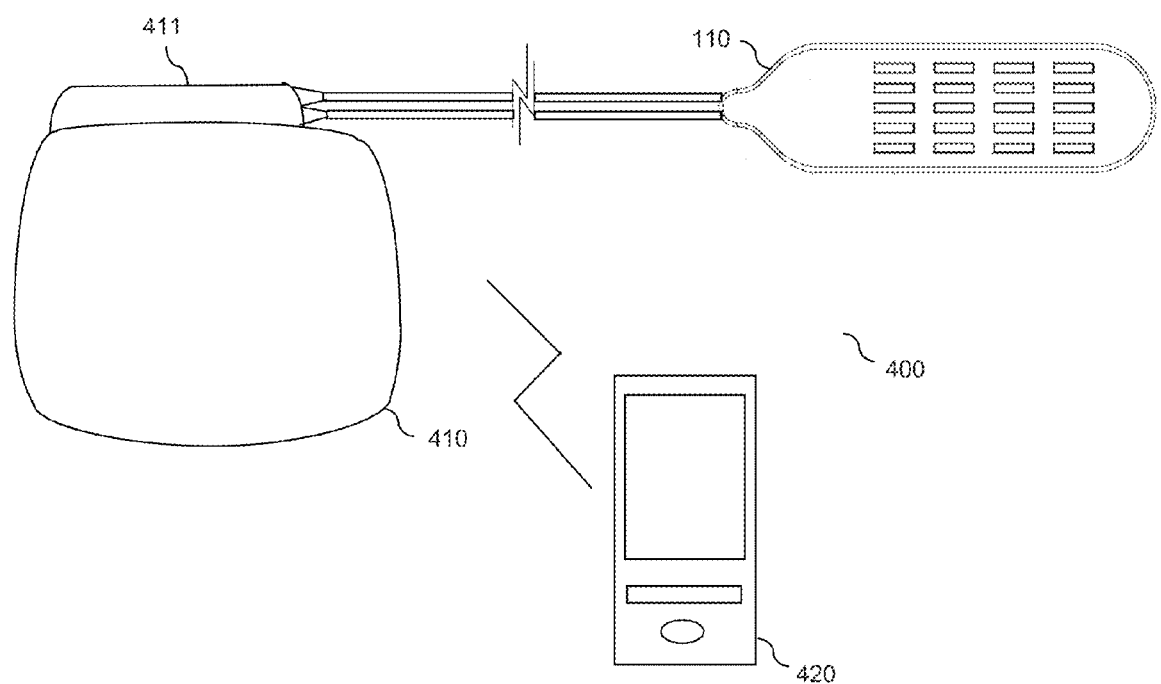
FIG. 4 depicts a stimulation system according to one representative embodiment.

FIG. 4 depicts stimulation system 400 according to one representative embodiment. System 400 includes paddle lead 110 coupled to IPG 410 which is in wireless communication with programmer device 420. An example of a commercially available IPG is the Eon® Rechargeable IPG available from Advanced Neuromodulation Systems, Inc., although any suitable IPG could be alternatively employed. As shown in FIG. 4, paddle lead 110 is coupled to header ports 411 of IPG 410. The electrical connectors within each header port 411 electrically couple respective terminals 118 of lead 110 to a switch matrix (not shown) within IPG 410.

The switch matrix selectively connects the pulse generating circuitry (not shown) of IPG 410 to the various terminals 118, and, hence to the electrodes 120. The sealed portion of IPG 410 contains the pulse generating circuitry, communication circuitry, control circuitry, and battery (not shown) within an enclosure to protect the components after implantation within a patient. The control circuitry may comprise a microprocessor, microcontroller, one or more ASICs, and/or any suitable circuitry for controlling the pulse generating circuitry. The control circuitry controls the pulse generating circuitry to apply electrical pulses to the patient via electrodes 120 of paddle 110 according to multiple pulse parameters (e.g., pulse amplitude, pulse width, pulse frequency, etc.). The electrodes 120 are set to function as cathodes or anodes or set to a high-impedance state for a given pulse according to the couplings provided by the switch matrix. The electrode states may be changed between pulses. Electrodes 120 are preferably processed to include laser machined trenches as discussed above. The surface characteristics of electrodes 120 permit increased current density relative to conventional electrodes and, hence, constant current pulses may be employed at higher levels than would be typically employed for similarly sized conventional electrodes.

When paddle lead 110 is initially implanted within the patient, a determination of the set(s) of pulse parameters and the electrode configuration(s) that effectively treat the patient's condition is made. The determination or programming typically occurs through a physician's interaction with stimulation therapy configuration software executed on the programmer device 420. The software steps the physician or clinician through a number of parameters and electrode configurations. In preferred embodiments, the electrode configurations are stepped through by "steering" the electrical field by moving the anodes and/or cathodes as discussed above. The patient provides feedback to the physician regarding the perceived stimulation that occurs in response to the pulse parameters and electrode configuration(s). The physician effects changes to the parameters and electrode configuration(s) until optimal pulse parameters and electrode configuration(s) are determined. The final pulse parameters and configurations are stored within IPG 410 for subsequent use. The pulse parameters and configurations are used by IPG 410 to control the electrical stimulation provided to the patient via paddle lead 410.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The invention claimed is:

1. A method of fabricating a stimulation lead for stimulating tissue of a patient, the method comprising:
   providing a lead body, the lead body comprising a plurality of conductors embedded within insulative material;
   providing a plurality of terminals;
   electrically coupling the plurality of terminals with the plurality of conductors;
   providing a plurality of electrodes, the plurality of electrodes comprising a plurality of substantially continuous longitudinal trenches on a surface of the electrodes, the electrodes comprising areas of reflow material forming conductive microstructures substantially continuously along walls of the longitudinal trenches;
   integrating the plurality of electrodes in a paddle structure; and
   electrically coupling the plurality of electrodes with the plurality of conductors.

2. The method of claim 1 wherein the plurality of electrodes are disposed in at least three columns on the paddle structure.

3. The method of claim 1 wherein the plurality of electrodes are ring electrodes and the longitudinal trenches circumscribe the plurality of electrodes.

4. The method of claim 1 wherein the plurality of electrodes are fabricated from platinum iridium alloy material.

5. The method of claim 1 wherein the trenches are approximately 0.04 inches wide.

6. The method of claim 1 wherein the areas of reflow material extend beyond confines of the longitudinal trenches.

7. The method of claim 1 wherein the areas of reflow material are substantially limited to confines of the longitudinal trenches.

8. The method of claim 1 further comprising;
   machining the plurality of electrodes to form the trenches on the plurality of electrodes by applying laser energy to the electrodes.

9. A stimulation lead for stimulating tissue of a patient, the stimulation lead comprising:
   a lead body comprising a plurality of conductors enclosed within insulative material;
   a plurality of terminals electrically coupled to the plurality of conductors;
   a plurality of electrodes electrically coupled to the plurality of conductors, wherein each electrode of the plurality of electrodes comprises a plurality of substantially continuous longitudinal trenches on a surface of the electrode, and each electrode comprises areas of reflow material forming conductive microstructures substantially continuously along walls of the longitudinal trenches; and
   a paddle structure with the plurality of electrodes disposed on the paddle structure.

10. The stimulation lead of claim 9 wherein the plurality of electrodes are disposed in at least five columns on the paddle structure.

11. The stimulation lead of claim 9 wherein the plurality of electrodes are ring electrodes and the longitudinal trenches circumscribe the plurality of electrodes.

12. The stimulation of claim 9 wherein the plurality of electrodes are fabricated from platinum iridium alloy material.

13. The stimulation of claim 9 wherein the trenches are approximately 0.04 inches wide.

14. The stimulation of claim 9 wherein the areas of reflow material extend beyond confines of the longitudinal trenches.

15. The stimulation of claim 9 wherein the areas of reflow material are substantially limited to confines of the longitudinal trenches.

* * * * *